United States Patent
Bergsma et al.

(10) Patent No.: US 6,297,036 B1
(45) Date of Patent: Oct. 2, 2001

(54) YAK-1 RELATED SERINE/THREONINE PROTEIN KINASE-HTLAR33

(75) Inventors: Derk Bergsma, Berwyn; Usman Shabon, Collegeville, both of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/271,815

(22) Filed: Mar. 18, 1999

Related U.S. Application Data

(62) Division of application No. 09/027,064, filed on Feb. 20, 1998.
(60) Provisional application No. 60/053,924, filed on Jul. 28, 1997.

(51) Int. Cl.⁷ .............................. C12N 9/12; C12N 15/00; C12N 7/20; C07K 1/00
(52) U.S. Cl. .................. 435/194; 435/320.1; 435/252.3; 435/325; 530/350
(58) Field of Search .................. 435/194, 320.1, 435/252.3, 325; 530/350

(56) References Cited

PUBLICATIONS

Garrett et al. "The *Saccharomyces cerevisiae* YAK1 Gene Encodes a Protein Kinase that Is Induced by Early in the Cell Cycle", Molecular and Cellular Biology, vol. 11 (8), pp. 4045–4052 (1991).

Tugendreich et al. "Linking yeast genetics to mammalian genomes: Identification and mapping of the Homolog of CDC27 via the expressed sequence tag (EST) data base", Proc. Natl. Acad. Sci. USA, vol. pp. 10031–10035 (1993).

Song et al. Isolation of Human and Murine Homologues of the Drosophila Minibrain Gene: Human Homologue Maps to 21q22.2 in the Down Syndrome "Critical Region", Genomics, vol. 38, pp. 331–339 (1996).

Copy of Partial EP Search Report.

Kentrup et al. "Dyrk, a dual specificity protein kinase with unique structural features whose activity is dependent on tyrosine residues between subdomains VII and VIII", J. Biol. Chem., vol. 271 (7), pp. 3488–3495 (1996).

Tejedor et al. "Minibrain: a new protein kinase family involved in postembryonic neurogenesis in Drosophila", Neuron, vol. 14 (2), pp. 287–301 (1995).

*Primary Examiner*—Rebecca E. Prouty
*Assistant Examiner*—Maryam Monshipouri
(74) *Attorney, Agent, or Firm*—William T. Han; Ratner & Prestia; William T. King

(57) ABSTRACT

HTLAR33 polypeptides and polynucleotides and methods for producing such polypeptides by recombinant techniques are disclosed. Also, disclosed are methods for utilizing HTLAR33 polypeptides and polynucleotides in therapy, and diagnostic assays for such.

6 Claims, No Drawings

YAK-1 RELATED SERINE/THREONINE PROTEIN KINASE-HTLAR33

This application is a division of U.S. application Ser. No. 09/027,064, filed, Feb. 20, 1998, which claims the benefit of U.S. Provisional Application No. 60/053,924, filed Jul. 28, 1997, both of whose contents are incorporated herein in their entireties.

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superceding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to HTLAR33, in particular HTLAR33 polypeptides and HTLAR33 polynucleotides, recombinant materials and methods for their production. In another aspect, the invention relates to methods for using such polypeptides and polynucleotides, including the treatment of bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, hereinafter referred to as "the Diseases", amongst others. In a further aspect, the invention relates to methods for identifying agonists and antagonists/inhibitors using the materials provided by the invention, and treating conditions associated with HTLAR33 imbalance with the identified compounds. In a still further aspect, the invention relates to diagnostic assays for detecting diseases associated with inappropriate HTLAR33 activity or levels.

DESCRIPTION OF THE INVENTION

In a first aspect, the present invention relates to HTLAR33 polypeptides. Such peptides include isolated polypeptides comprising an amino acid sequence which has at least 70% identity, preferably at least 80% identity, more preferably at least 90% identity, yet more preferably at least 95% identity, most preferably at least 97–99% identity, so that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the Serine/Threonine Protein kinase family of polypeptides. They are therefore of interest because a number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein serine/threonine kinases (PSTK) and phosphatases. Serine/threonine phosphorylation is a major mediator of signal transduction in multicellular organisms. Receptor-bound, membrane-bound and intracellular PSTKs regulate cell proliferation, cell differentiation and signalling processes in many cell types.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are potential targets for drug design.

A subset of PSTKs are involved in regulation of cell cycling. These are the cyclin-dependent kinases or CDKs (Peter and Herskowitz, Cell 1994:79, 181–184). CDKs are activated by binding to regulatory proteins called cyclins and control passage of the cell through specific cell cycle checkpoints. For example, CDK2 complexed with cyclin E allows cells to progress through the G1to S phase transition. The complexes of CDKs and cyclins are subject to inhibition by low molecular weight proteins such as p16 (Serrano et al, Nature 1993:366, 704), which binds to and inhibits CDK4. Deletions or mutations in p16 have been implicated in a variety of tumors (Kamb et al, Science 1994:264, 436–440). Therefore, the proliferative state of cells and diseases associated with this state are dependent on the activity of CDKs and their associated regulatory molecules. In diseases such as cancer where inhibition of proliferation is desired, compounds that inhibit CDKs may be useful therapeutic agents. Conversely, activators of CDKs may be useful where enhancement of proliferation is needed, such as in the treatment of immunodeficiency.

YAK1, a PSTK with sequence homology to CDKs, was originally identified in yeast as a mediator of cell cycle arrest caused by inactivation of the cAMP-dependent protein kinase PKA (Garrett et al, Mol Cell Biol. 1991:11, 4045–4052). YAK1 kinase activity is low in cycling yeast but increases dramatically when the cells are arrested prior to the S-G2transition. Increased expression of YAK1 causes growth arrest in yeast cells deficient in PKA. Therefore, YAK1 can act as a cell cycle suppressor in yeast.

Frequently, in diseases such as osteoporosis and osteoarthritis, patients have established lesions of bone or cartilage, respectively. Treatment of such lesions requires an agent that will stimulate new bone or cartilage formation to replace that lost to the disease. Therefore, there is a need for drugs that increase the number of osteoblasts or chondrocytes, the cells responsible for bone or cartilage formation, respectively. Similarly, replacement of heart or skeletal muscle depleted by diseases such as myocardial infarction or HIV-associated cachexia requires drugs that stimulate proliferation of cardiac myocytes or skeletal myoblasts. The present invention describes a novel human homolog of yeast YAK1 termed HTLAR33. The sequence of HTLAR33 shares homology with predicted PSTK's from D. melanogaster, human and R. norvegicus and has motifs associated with known protein kinases. Inhibitors of HTLAR33 are expected to stimulate proliferation of cells in which it is expressed. These properties are hereinafter referred to as "HTLAR33 activity" or "HTLAR33 polypeptide activity" or "biological activity of HTLAR33". Also included amongst these activities are antigenic and immunogenic activities of said HTLAR33 polypeptides, in particular the antigenic and immunogenic activities of the polypeptide of SEQ ID NO:2. Preferably, a polypeptide of the present invention exhibits at least one biological activity of HTLAR33.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to HTLAR33 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with D. melanogaster serine/threonine protein kinase (F. Tejedor, et. al., Neuron 14(2):287–301, 1995). The nucleotide sequence of SEQ ID NO:1 is a cDNA sequence and comprises a polypeptide encoding sequence (nucleotide 209 to 1883) encoding a polypeptide of 558 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the Serine/Threonine Protein kinase family, having homology and/or structural similarity with R. norvegicus Dual Specificity Yak-1 related Kinase (Dyrk) (H. Kentrup, et. al. J. Biol. Chem, 271(7):3488–3495, 1996).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one HTLAR33 activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide comprising:
(a) a nucleotide sequence which has at least 70% identity, preferably at lest 80% identity, more preferably at least 90% identity, yet more preferably at least 95% identity, even more preferably at least 97–99% identity to SEQ ID NO:3 over the entire length of SEQ ID NO:3;
(b) a nucleotide sequence which has at least 70% identity, preferably at least 80% identity, more preferably at least 90% identity, yet more preferably at least 95% identity, even more preferably at least 97–99% identity, to SEQ ID NO:1 over the entire length of SEQ ID NO:3;

(c) the polynucleotide of SEQ ID NO:3; or (d) a nucleotide sequence encoding a polypeptide which has at least 70% identity, preferably at least 80% identity, more preferably at least 90% identity, yet more preferably at least 95% identity, even more preferably at least 97–99% identity, to the amino acid sequence of SEQ ID NO:4, over the entire length of SEQ ID NO:4;

as well as the polynucleotide of SEQ ID NO:3.

The present invention further provides for a polypeptide which:

(a) comprises an amino acid sequence which has at least 70% identity, preferably at least 80% identity, more preferably at least 90% identity, yet more preferably at least 95% identity, most preferably at least 97–99% identity, so that of SEQ ID NO:2 over the entire length of SEQ ID NO:4;

(b) has an amino acid sequence which is at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:4;

(c) comprises the amino acid of SEQ ID NO:4; and (d) is the polypeptide of SEQ ID NO:4;

as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained using standard cloning and screening techniques, from a cDNA library derived from mRNA in cells of human brain using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989)86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of SEQ ID NO:1 or a fragment thereof, and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™' technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran medicated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characterised by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HTLAR33 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee. e.g., Myers et al., *Science* (1985) 230:1242). Sequence changes at specific locations may also be revealed by nuclease protections assays, such as RNase and S1 protection or the chemical cleavage method (see Cotton et al., *Proc Natl Acad Sci USA* (1985) 85:4397–4401). In another embodiment, an array of oligonucleotides probes comprising HTLAR33 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al.,Science, Vol 274, pp 610–613 (1996)).

The diagnostic assays offer a process for diagnosing or determining a susceptibility to the Diseases through detection of mutation in the HTLAR33 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:
  (a) a polynucleotide of the present invention, preferably the nucleotide sequence of SEQ ID NO:1, or a fragment thereof;
  (b) a nucleotide sequence complementary to that of (a);
  (c) a polypeptide of the present invention, preferably the polypeptide of SEQ ID NO:2 or a fragment thereof; or
  (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease of suspectability to a disease, particularly bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington3 s disease or Gilles dela Tourett's syndrome, amongst others.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried conditions requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for many biological functions, including many disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., *Current Protocols in Immunology* 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polpypeptides maybe employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring HTLAR33 activity in the mixture, and comparing the HTLAR33 activity of the mixture to a standard. Fusion proteins, such as those made from Fc portion and HTLAR33 polypeptide, as hereinbefore described, can also be used for high-throughput screening assays to identify antagonists for the polypeptide of the present invention (see D. Bennett et al., J. Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies, or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention; which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesing candidate compounds that are predicted to bind to or react with the deduced binding or reactive site; and (d) testing whether the candidate compounds are indeed agonists, antagonists or inhibitors.

It will be further appreciated that this will normally be an interactive process.

In a further aspect, the present invention provides methods of treating abnormal conditions such as, for instance, bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease of Gilles dela Tourett's syndrome, related to either an excess of, or an under-expression of, HTLAR33 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal conditions. In another approach, soluble forms of the polypeptides still capable of binding the ligand, substrate, enzymes, receptors, etc. in competition with endogenous polypeptide may be administered. Typical examples of such competitors include fragments of the HTLAR33 polypeptide.

In still another approach, expression of the gene encoding endogenous HTLAR33 polypeptide can be inhibited using expression blocking techniques. Known such techniques involve the use of antisense sequences, either internally generated or separately administered (see, for example. O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 2512:1360). These oligomers can be administered per se or the relevant oligomers can be expressed in vivo.

For treating abnormal conditions related to an under-expression of HTLAR33 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of HTLAR33 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells maybe administered to a subject for engineering cells in vivo and expression of the polypeptide in vivo. For an overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration . For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains. generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques (see, e.g.: COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton D., *SIAM J Applied Math* (1988) 48:1073. Methods to determine identity and similarity are codified in computer programs. Preferred computer program methods to determine identity and similarity between two sequences include, but are not limited to, GCG program package (Devereux, J., et al., *Nucleic Acids Research* (1984) 12(1):387), BLASTP, BLASTN, and FASTA (Atschul, S. F. et al., *J Molec Biol* (1990) 215:403).

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletions, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y)$$

wherein $n_n$ is the number of nucleotide alterations, $x_n$ is the total number of nucleotides in SEQ ID NO:1, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y)$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer produce of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

EXAMPLE 1

Random nucleotide searches of a commercial EST database resulted in identification of a 180 bp EST, (EST NO 396208) which showed significant homology to Yak-1related kinases. This clone was further analysed by sequencing. The partial clone had an insert of 1338 bp (SEQ ID NO:3), with a single open reading frame that encoded for a polypeptide of 412 amino acid residues (SEQ ID NO:4). Using gene specific primers (5'-GATCTTGATGGCCACAAGCTCCTGGGT-3' (SEQ ID NO:5) and 5'-GTCAATTTCGTAGCGCTCCACCAGCGCT-3' (SEQ ID NO:6).) and human Brian Marathon cDNA (Clontech, Palo Alto, Calif.), PCR fragments corresponding to the missing 5' region were obtained. This region was confirmed by obtaining the same fragment from human skeletal muscle tissue cDNA. The final 2394 bp clone encodes for Serine/threonine kinase and has very high homology to other members of STK family.

```
                        SEQUENCE INFORMATION
  1    GTGAGAAAGG GATTTGACAT GGGGGAGACA GTGGCCCATG GGGAGAAgAT SEQ ID NO:1

51    TTTTGCTGTA CCTGACAACT CTGGGAGGAG AGAACCCTAT GTGATAACTT

101    GGGGATTTGA CTTTGAGGCC CTCTAGGATG GACACaGTTG TGGAATGACC

151    CTGGTATAAA AGGGGTGCCT GGAGAAAgGT CTCAGCGGCG GTGGCgCCgA

201    GGTGCACGAT GCAAGAAGGC GCCCCCCGGC CGGGCTCCCG CTCCAGGCCT

251    GGTTCCCATG GGCCcTcTGA GCCCACCATG GCcGTCCCAC CGGGCCATGG

301    TCCcTTCTCT GGCTTCCCAG GGCCCCAGGA GCACACGCAG GTATTGCCTG

351    ATGTGCGGcT ACTGCCTCGG AGGCTGCCCC TGGCCTTCCG GGATGCAACC

401    TCAGCCCGCT GGGTAAGCTC TCTGTGCCTC ATCAAGACCT ACAAGCACAT
```

-continued

```
 451 CAATGAGGTA TACTATGCGA AGAAGAAGCG GCGGGCCCAG CAGGGCCACC
 501 CCAGGATTGG AGCAAACAAG AAGGAGAAGA AGGTCcTGAA CCATGGTTAT
 551 GATGAGGACA ACCATGATAA CATCGTGGCG CAGTGGCGAG CGCTGGTGGA
 601 GCGCTACGAA ATTGACTCGC TCATTGGCAA AGGCTCCTTT GGCCAGGTGG
 651 TGAAAGCCTA TGATCATCAG ACCCAGGAGC TTGTGGCCAT CAAGATCATC
 701 AAGAACAAAA AGGCTTTCCT GAACCAGGCC CAGATTGAGC TGCGGCTGCT
 751 GGAGCTGATG AACCAGCATG ACACGGAGAT GAAGTACTAT ATAGTACACC
 801 TGAAGCGGCA CTTCATGTTC CGGAACCACC TGTGCCTGGT ATTTGAGCTG
 951 CTGTCCTACA ACCTGTACGA CCTCCTGCGC AACACCCACT TCCGCGGCGT
 901 CTCGCTGAAC CTGACCCGGA AGCTGGCGCA GCAGCTCTGC ACGGCACTGC
 951 TCTTTCTGGC CACGCCTGAG CTCAGCACCA TTCACTGCGA CCTCAAGCCC
1001 GAAACATCT TGCTGTGCAA CCCCAAGCGC AGCGCCATCA AGATTGTGGA
1051 CTTCGGCAGC TCCTGCCAGC TTGGCCAGAG GATCTACCAG TATATCCAGA
1101 GCCGCTTCTA CCGCTCACCT GAGGTGCTCC TGGGCACACC CTACGACCTG
1151 GCCATTGACA TGTGGTCCCT GGGCTGCATC CTTGTGGAGA TGCACACCGG
1201 AGAGCCCCTC TTCAGTGGCT CCAATGAGGT CGACCAGATG AACCGCATTG
1251 TGGAGGTGCT GGGCATCCCA CCGGCCGCCA TGCTGGACCA GGCGCCCAAG
1301 GCTCGCAAGT ACTTTGAACG GCTGCCTGGG GGTGGCTGGA CCCTACgAAG
1351 GACGAAAGAA CTCAGGAAGG ACCTGGTGCT GCGCATGCTG GAGTATGAGC
1401 CCGCCGCCCG CATCAGCCCC CTGGGGGCTC TGCAGCACGC CTTCTTCCGC
1451 CGCACGGCCG ACGAAGCCAC CAACACGGGC CCGGCAGGCA GCAGTGcCTC
1501 CACCTCGCCC GCGCCCCCCG ACACCTGCCC CTCTTCCAGC ACCGCCAGCT
1551 CGGAGGCTCC AGTGGCTCCT CCAGTGACAA CCGGACCGAT ATTGTGGGGG
1601 CCCTGGGCCC CCTATCACAG ACTGCCCCCA GGTCCCACCC TCCCAGCCGC
1651 TGCGGCGTGC CCCACAAGAC ACATCAAGCC CCTGCCTCTG CCTCGTCACT
1701 GCCTGGGAAC GGGGCCCAgT TACCCCCCCA GCCCGATACT TGGTCGTCCC
1751 CATCACCAAC cCTCACCACC ACCCCCGGAG CTGATGGATG TGAGCCTGGT
1801 GGGCGGCCtG CTGACTGCTC CCCACCTCAC CCAGCGCCTG CCCCCCAgCA
1851 CCCGGCTGCC TCAGCCCTCC GGACTCGGAT GACTGGAGGT CGTCCACCCC
1901 TCCCGCCTCC TGATGACCCT GCCACTCTGG GGCCTCaCCT GGCCTCCGTG
1951 GTGTACCCCA GAGCACAGCA GCCAGCTCGT GACCCTGCCC CCTCCCTGGG
2001 GCCCCTCCTG AAAGCCATAC.CCTCCCCCAT CTGGGGGCCC TGgGCTCCCA
2051 TCCTCATCTC TCTCCTTGAC TGGAATTGCT GCTACCCAgC TGGGGTGGGT
2101 GAGGCCTGCA CTGATCGGGG CCTGGGGCAG GGGGGTCAAG GAGAGGGTTT
2151 TGGCCGCTC C CTC CCCACTA AGGACTGGAC CCTTGGGCCC CTcTC-
     CCCCT
2201 TTTTTTCTAT TTATTGTACC AAAGACAGTG GTGGTCCGGT GGAGGGAAGA
2251 CCCCCCCCTC ACCCCAGGAC CCTAGGAGGG GGTGGGGGCA GGTAGGGGGA
2301 GATGGCCTTG CTCCTCCTCG CTGTACCCCC AGTAAAGAGC TTTCTCACAA
2351 AAAAAAAAAA AAAAAAACTC GAGGGGGGCC CGTACCCAAT CGCC

1 MQEGAPRPGS RSRPG5HGFS EPTMAVPPGH GPFSGFPGPQ EHTQVLPDVR SEQ ID NO:2
```

```
 51  LLPRRLPLAF RDATSARWVS SLCLIKTYKH INEVYYAKKK RRAQQGHPRI

101  GANKKEKKVL NHGYDEDNHD NIVAQWRALV ERYEIDSLIG KGSFGQVVKA

151  YDHQTQELVA IKIIKNKKAF LNQAQIELRL LELMNQHDTE MKYYIVHLKR

201  HFMFRNHLCL VFELLSYNLY DLLRNTHFRG VSLNLTRKLA QQLCTALLFL

251  ATPELSIIHC DLKPENILLC NPKRSAIKIV DFGSSCQLGQ RIYQYIQSRF

301  YRSPEVLLGT PYDLAIDMWS LGCILVEMHT GEPLFSGSNE VDQMNRIVEV

351  LGIPPAAMLD QAPKARKYFE RLFGGGWTLR RTKELRKDLV LFMLEYEPAA

401  RISPLGALQH GFFRRTADEA TNTGFAGSSA STSPAPLDTC PSSSTASSEA

451  PVAPPVTTGP ILWGFWAPYH RLPPGPTLPA AAACPTRHIK PLPLPRHCLG

501  TGPSYPPSPI LGRPHHQPSP FPPELMDVSL VGGLLTAPHL TQRLPPSTRL

551  PQPSGLG

1  GAATTCGGCA CGAGCCTGGG CACACCCTAC GACCTGGCCA TTGACATGTG    SEQ ID NO:3

51  GTCCCTGGGC TGCATCCTTG TGGAGATGCA CACCGGAGAG CCCCTCTTCA

101  GTGGCTCCAA TGAGGTCGAC CAGATGAACC GCATTGTGGA GGTGCTGGGC

151  ATCCCACCGG CCGCCATGCT GGACCAGGCG CCCAAGGCTC GCAAGTACTT

201  TGAACGGCTG CCTGGGGGTG GCTGGACCCT ACGAAGGACG AAAGAACTCA

251  GGAAGGACCT GGTGCTGCGC ATGCTGGAGT ATGAGCCCGC CGCCCGCATC

301  AGCCCCCTGG GGGCTCTGCA GCACGGCTTC TTCCGCCGCA CGGCCGACGA

351  AGCCACCAAC ACGGGCCCGG CAGGCAGCAG TGCCTCCACC TCGCCCCCGC

401  CCCTCGACAC CTGCCCCTCT TCCAGCACCG CCAGCTCCAT CTCCAGTTCT

451  GGAGGCTCCA GTGGCTCCTC CAGTGACAAC CGGACCTACC GCTACAGCAA

501  CCGATATTGT GGGGGCCCTG GGCCCCCTAT ACAGACTGT GAGATGAACA

551  GCCCCCAGGT CCCACCCTCC CAGCCGCTGC GGCCCTGGGC AGGGGGTGAT

601  GTGCCCCACA AGACACATCA AGCCCCTGCC TCTGCCTCGT CACTGCCTGG

651  GAACGGGGCC CAGTTACCCC CCCAGCCCGA TACTTGGTCG TCCCCATCAC

701  CAACCCTCAC CACCACCCCC GGAGCTGATG GATGTGAGCC TGGTGGGCGG

751  CCTGCTGACT GCTCCCCACC TCACCCAGCG CCTGCCCCCC AGCACCCGGC

801  TGCCTCAGCC CTCCGGACTC CGATGACTGG AGGTCGTCCA CCCCTCCCGC

851  CTCCTGATGA CCCTGCCACT CTGGGGCCTC ACCTGGCCTC CGTGGTGTAC

901  CCCAGAGCAC AGCAGCCAGC TCGTGACCCT GCCCCCTCCC TGGGGCCCCT

951  CCTGAAAGCC ATACCCTCCC CCATCTGGGG GCCCTGGGCT CCCATCCTCA

1001 TCTCTCTCCT TGACTGGAAT TGCTGCTACC CAGCTGGGGT GGGTGAGGCC

1051 TGCACTGATT GGGGCCTGGG GCAGGGGGGT CAAGGAGAGG GTTTTGGCCG

1101 CTCCCTCCCC ACTAAGGACT GGACCCTTGG GCCCCTCTCC CCCTTTTTTT

1151 CTATTTATTG TACCAAAGAC AGTGGTGGTC CGGTGGAGGG AAGACCCCCC

1201 CCTCACCCCA GGACCCTAGG AGGGGTGGG GGCAGGTAGG GGGAGATGGC

1251 CTTGCTCCTC CTCGCTGTAC CCCCAGTAAA GAGCTTTCTC ACAAAAAAA

1301 AAAAAAAAA ACTCGAGGGG GGCCCGTACC CAATCGCC

1  EFGTSLGTPY DLAIDMWSLG CILVEMHTGE PLFSGSNEVD QMNRIVEVLG    SEQ ID NO:4

51  IPPAAMLDQA PKARKYFERL PGGGWTLRRT KELRKDLVLR MLEYEPAARI
```

-continued

```
101  SPLGALQHGF FRRTADEATN TGPAGSSAST SPAPLDTCPS SSTASSISSS

151  GGSSGSSSDN RTYRYSNRYC GGPGFPITDC EMNSPQVPPS QFLRPWAGGD

201  VPHKTHQAPA SASSLPGNGA QLPPQPDTWD SPSPTLTTTP GADGCEPGGR

251  PADCSPPHPA PAPQHPAASA LRTRMTGGRP PLPPPDDPAT LGPHLASVVY

301  PPAQQPARDP APSLGPLLKA IPSPIWGPWA PILISLLDWN CCYPAGVGEA

351  CTDWGLGQGG QGEGFGRSLF TKDWTLGFLS PFFSIYCTKD SGGPVEGRPP

401  PHPRTLGGGG GR
```

What is claimed is:

1. An isolated polypeptide having at least 70% identity to the amino acid sequence of SEQ ID NO:2 over the entire length of SEQ ID NO:2, wherein said polypeptide has serine/threonine kinase activity.

2. An isolated polypeptide having at least 80% identity to the amino acid sequence of SEQ ID NO:2 over the entire length of SEQ ID NO:2, wherein said polypeptide has serine/threonine kinase activity.

3. An isolated polypeptide having at least 90% identity to the amino acid sequence of SEQ ID NO:2 over the entire length of SEQ ID NO:2, wherein said polypeptide has serine/threonine kinase activity.

4. An isolated polypeptide having at least 95% identity to the amino acid sequence of SEQ ID NO:2 over the entire length of SEQ ID NO:2, wherein said polypeptide has serine/threonine kinase activity.

5. An isolated polypeptide comprising the amino acid sequence of SEQ ID NO:2.

6. An isolated polypeptide consisting of the amino acid sequence of SEQ ID NO:2.

* * * * *

SEQUENCE LISTING

<160> NUMBER OF SEQ ID NOS: 6

<210> SEQ ID NO 1
<211> LENGTH: 2394
<212> TYPE: DNA
<213> ORGANISM: Homo sapiens

<400> SEQUENCE: 1

```
gtgagaaagg gatttgacat gggggagaca gtggcccatg gggagaagat ttttgctgta     60
cctgacaact ctgggaggag agaaccctat gtgataactt ggggatttga ctttgaggcc    120
ctctaggatg gacacagttg tggaatgacc ctggtataaa aggggtgcct ggagaaaggt    180
ctcagcggcg gtggcgccga ggtgcacgat gcaagaaggc gccccccggc cgggctcccg    240
ctccaggcct ggttcccatg ggccctctga gcccaccatg gccgtccact cgggccatgg    300
tcccttctct ggcttcccag ggccccagga gcacacgcag gtattgcctg atgtgcggct    360
actgcctcgg aggctgcccc tggccttccg ggatgcaacc tcagcccgct gggtaagctc    420
tctgtgcctc atcaagacct acaagcacat caatgaggta tactatgcga agaagaagcg    480
gcgggcccag cagggccacc ccaggattgg agcaaacaag aaggagaaga aggtcctgaa    540
ccatggttat gatgaggaca accatgataa catcgtggcg cagtggcgag cgctggtgga    600
gcgctacgaa attgactcgc tcattggcaa aggctccttt ggccaggtgg tgaaagccta    660
tgatcatcag acccaggagc ttgtggccat caagatcatc aagaacaaaa aggctttcct    720
gaaccaggcc cagattgagc tgcggctgct ggagctgatg aaccagcatg acacggagat    780
gaagtactat atagtacacc tgaagcggca cttcatgttc cggaaccacc tgtgcctggt    840
atttgagctg ctgtcctaca acctgtacga cctcctgcgc aacacccact ccgcggcgt    900 ctcgctgaac ctgacccgga agctggcgca gcagctctgc acggcactgc tctttctggc    960
cacgcctgag ctcagcatca ttcactgcga cctcaagccc gaaaacatct tgctgtgcaa   1020
ccccaagcgc agcgccatca gattgtggac cttcggcagc tcctgccagc ttggccagag   1080
gatctaccag tatatccaga gccgcttcta ccgctcacct gaggtgctcc tgggcacacc   1140
ctacgacctg gccattgaca tgtggtccct gggctgcatc cttgtggaga tgcacaccgg   1200
agagcccctc ttcagtggct ccaatgaggt cgaccagatg aaccgcattg tggaggtgct   1260
gggcatccca ccggccgcca tgctggacca ggcgcccaag gctcgcaagt actttgaacg   1320
gctgcctggg gtggctggac cctacgaaga cgaaagaa ctcaggaagg acctggtgct    1380
gcgcatgctg gagtatgagc ccgccgcccg catcagcccc ctgggggctc tgcagcacgg   1440
cttcttccgc cgcacggccg acgaagccac caacacgggc ccggcaggca gcagtgcctc   1500
```

```
cacctcgccc gcgcccctcg acacctgccc ctcttccagc accgccagct cggaggctcc    1560
agtggctcct ccagtgacaa ccggaccgat attgtggggg ccctgggccc cctatcacag    1620
actgccccca ggtcccaccc tcccagccgc tgcggcgtgc cccacaagac acatcaagcc    1680
cctgcctctg cctcgtcact gcctgggaac ggggcccagt tacccccca gcccgatact     1740 tggtcgtccc catcaccaac cctcaccacc accccggag ctgatggatg tgagcctggt     1800
gggcggcctg ctgactgctc cccacctcac ccagcgcctg cccccagca cccggctgcc     1860 tcagccctcc ggactcggat gactggaggt cgtccacccc tcccgcctcc tgatgaccct    1920
gccactctgg ggcctcacct ggcctccgtg gtgtacccca gagcacagca gccagctcgt    1980
gaccctgccc cctccctggg gcccctcctg aaagccatac cctcccccat ctggggggccc   2040 tgggctccca tcctcatctc tctccttgac tggaattgct gctacccagc tggggtgggt    2100
gaggcctgca ctgattgggg cctggggcag ggggtcaag gagagggttt tggccgctcc    2160
ctccccacta aggactggac ccttgggccc ctctcccct ttttttctat ttattgtacc     2220
aaagacagtg gtggtccggt ggagggaaga ccccccctc accccaggac cctaggaggg     2280
ggtgggggca ggtaggggga gatggccttg ctcctcctcg ctgtaccccc agtaaagagc    2340
tttctcacaa aaaaaaaaaa aaaaaaactc gagggggggcc cgtacccaat cgcc         2394
```

<210> SEQ ID NO 2
<211> LENGTH: 557
<212> TYPE: PRT
<213> ORGANISM: Homo sapiens

<400> SEQUENCE: 2

```
Met Gln Glu Gly Ala Pro Arg Pro Gly Ser Arg Ser Arg Pro Gly Ser
 1               5                  10                  15

His Gly Pro Ser Glu Pro Thr Met Ala Val Pro Pro Gly His Gly Pro
            20                  25                  30

Phe Ser Gly Phe Pro Gly Pro Gln Glu His Thr Gln Val Leu Pro Asp
        35                  40                  45

Val Arg Leu Leu Pro Arg Arg Leu Pro Leu Ala Phe Arg Asp Ala Thr
    50                  55                  60

Ser Ala Arg Trp Val Ser Ser Leu Cys Leu Ile Lys Thr Tyr Lys His
65                  70                  75                  80

Ile Asn Glu Val Tyr Tyr Ala Lys Lys Lys Arg Arg Ala Gln Gln Gly
                85                  90                  95

His Pro Arg Ile Gly Ala Asn Lys Lys Glu Lys Lys Val Leu Asn His
            100                 105                 110

Gly Tyr Asp Glu Asp Asn His Asp Asn Ile Val Ala Gln Trp Arg Ala
        115                 120                 125

Leu Val Glu Arg Tyr Glu Ile Asp Ser Leu Ile Gly Lys Gly Ser Phe
    130                 135                 140

Gly Gln Val Val Lys Ala Tyr Asp His Gln Thr Gln Glu Leu Val Ala
145                 150                 155                 160

Ile Lys Ile Ile Lys Asn Lys Lys Ala Phe Leu Asn Gln Ala Gln Ile
                165                 170                 175

Glu Leu Arg Leu Leu Glu Leu Met Asn Gln His Asp Thr Glu Met Lys
            180                 185                 190

Tyr Tyr Ile Val His Leu Lys Arg His Phe Met Phe Arg Asn His Leu
        195                 200                 205

Cys Leu Val Phe Glu Leu Leu Ser Tyr Asn Leu Tyr Asp Leu Leu Arg
```

```
        210                 215                 220
Asn Thr His Phe Arg Gly Val Ser Leu Asn Leu Thr Arg Lys Leu Ala
225                 230                 235                 240

Gln Gln Leu Cys Thr Ala Leu Leu Phe Leu Ala Thr Pro Glu Leu Ser
                245                 250                 255

Ile Ile His Cys Asp Leu Lys Pro Glu Asn Ile Leu Leu Cys Asn Pro
            260                 265                 270

Lys Arg Ser Ala Ile Lys Ile Val Asp Phe Gly Ser Ser Cys Gln Leu
        275                 280                 285

Gly Gln Arg Ile Tyr Gln Tyr Ile Gln Ser Arg Phe Tyr Arg Ser Pro
    290                 295                 300

Glu Val Leu Leu Gly Thr Pro Tyr Asp Leu Ala Ile Asp Met Trp Ser
305                 310                 315                 320

Leu Gly Cys Ile Leu Val Glu Met His Thr Gly Glu Pro Leu Phe Ser
                325                 330                 335

Gly Ser Asn Glu Val Asp Gln Met Asn Arg Ile Val Glu Val Leu Gly
            340                 345                 350

Ile Pro Pro Ala Ala Met Leu Asp Gln Ala Pro Lys Ala Arg Lys Tyr
        355                 360                 365

Phe Glu Arg Leu Pro Gly Gly Gly Trp Thr Leu Arg Arg Thr Lys Glu
    370                 375                 380

Leu Arg Lys Asp Leu Val Leu Arg Met Leu Glu Tyr Glu Pro Ala Ala
385                 390                 395                 400

Arg Ile Ser Pro Leu Gly Ala Leu Gln His Gly Phe Phe Arg Arg Thr
                405                 410                 415

Ala Asp Glu Ala Thr Asn Thr Gly Pro Ala Gly Ser Ser Ala Ser Thr
            420                 425                 430

Ser Pro Ala Pro Leu Asp Thr Cys Pro Ser Ser Ser Thr Ala Ser Ser
        435                 440                 445

Glu Ala Pro Val Ala Pro Val Thr Thr Gly Pro Ile Leu Trp Gly
    450                 455                 460

Pro Trp Ala Pro Tyr His Arg Leu Pro Pro Gly Pro Thr Leu Pro Ala
465                 470                 475                 480

Ala Ala Ala Cys Pro Thr Arg His Ile Lys Pro Leu Pro Leu Pro Arg
                485                 490                 495

His Cys Leu Gly Thr Gly Pro Ser Tyr Pro Pro Ser Pro Ile Leu Gly
            500                 505                 510

Arg Pro His His Gln Pro Ser Pro Pro Pro Glu Leu Met Asp Val
        515                 520                 525

Ser Leu Val Gly Gly Leu Leu Thr Ala Pro His Leu Thr Gln Arg Leu
    530                 535                 540

Pro Pro Ser Thr Arg Leu Pro Gln Pro Ser Gly Leu Gly
545                 550                 555

<210> SEQ ID NO 3
<211> LENGTH: 1338
<212> TYPE: DNA
<213> ORGANISM: Homo sapiens

<400> SEQUENCE: 3
gaattcggca cgagcctggg cacaccctac gacctggcca ttgacatgtg gtccctgggc    60
tgcatccttg tggagatgca caccggagag cccctcttca gtggctccaa tgaggtcgac   120
cagatgaacc gcattgtgga ggtgctgggc atcccaccgg ccgccatgct ggaccaggcg   180
```

```
cccaaggctc gcaagtactt tgaacggctg cctgggggtg gctggaccct acgaaggacg      240
aaagaactca ggaaggacct ggtgctgcgc atgctggagt atgagcccgc cgcccgcatc      300 agcccctgg ggctctgca gcacggcttc ttccgccgca cggccgacga agccaccaac       360
acgggcccgg caggcagcag tgcctccacc tcgcccgcgc cctcgacac ctgcccctct       420 tccagcaccg ccagctccat ctccagttct ggaggctcca gtggctcctc cagtgacaac      480
cggacctacc gctacagcaa ccgatattgt ggggccctg gccccctat acagactgt        540 gagatgaaca ccccccaggt cccaccctcc cagccgctgc ggccctgggc aggggtgat      600 gtgccccaca agacacatca agccctgcc tctgcctcgt cactgcctgg aacggggcc       660 cagttacccc cccagcccga tacttggtcg tccccatcac caaccctcac caccaccccc      720
ggagctgatg gatgtgagcc tggtgggcgg cctgctgact gctccccacc tcacccagcg      780
cctgcccccc agcacccggc tgcctcagcc ctccggactc ggatgactgg aggtcgtcca      840
cccctcccgc ctcctgatga ccctgccact ctggggcctc acctggcctc cgtggtgtac      900
cccagagcac agcagccagc tcgtgaccct gcccctccc tggggcccct cctgaaagcc       960 atacccctccc ccatctgggg gccctgggct cccatcctca tctctctcct tgactggaat   1020
tgctgctacc cagctggggt gggtgaggcc tgcactgatt ggggcctggg gcaggggggt    1080
caaggagagg gttttggccg ctccctcccc actaaggact ggaccttgg gccctctcc     1140 cccttttttt ctatttattg taccaaagac agtggtggtc cggtggaggg aagacccccc    1200
cctcacccca ggaccctagg aggggtggg ggcaggtagg gggagatggc cttgctcctc     1260
ctcgctgtac cccagtaaa gagctttctc acaaaaaaaa aaaaaaaaaa actcgagggg   1320
ggcccgtacc caatcgcc                                                 1338
```

<210> SEQ ID NO 4
<211> LENGTH: 412
<212> TYPE: PRT
<213> ORGANISM: Homo sapiens

<400> SEQUENCE: 4

Glu Phe Gly Thr Ser Leu Gly Thr Pro Tyr Asp Leu Ala Ile Asp Met
1               5                   10                  15

Trp Ser Leu Gly Cys Ile Leu Val Glu Met His Thr Gly Glu Pro Leu
            20                  25                  30

Phe Ser Gly Ser Asn Glu Val Asp Gln Met Asn Arg Ile Val Glu Val
        35                  40                  45

Leu Gly Ile Pro Pro Ala Ala Met Leu Asp Gln Ala Pro Lys Ala Arg
    50                  55                  60

Lys Tyr Phe Glu Arg Leu Pro Gly Gly Gly Trp Thr Leu Arg Arg Thr
65                  70                  75                  80

Lys Glu Leu Arg Lys Asp Leu Val Leu Arg Met Leu Glu Tyr Glu Pro
                85                  90                  95

Ala Ala Arg Ile Ser Pro Leu Gly Ala Leu Gln His Gly Phe Phe Arg
            100                 105                 110

Arg Thr Ala Asp Glu Ala Thr Asn Thr Gly Pro Ala Gly Ser Ser Ala
        115                 120                 125

Ser Thr Ser Pro Ala Pro Leu Asp Thr Cys Pro Ser Ser Ser Thr Ala
    130                 135                 140

```
Ser Ser Ile Ser Ser Gly Gly Ser Ser Gly Ser Ser Asp Asn
145                 150                 155                 160

Arg Thr Tyr Arg Tyr Ser Asn Arg Tyr Cys Gly Gly Pro Gly Pro Pro
                165                 170                 175

Ile Thr Asp Cys Glu Met Asn Ser Pro Gln Val Pro Pro Ser Gln Pro
            180                 185                 190

Leu Arg Pro Trp Ala Gly Gly Asp Val Pro His Lys Thr His Gln Ala
        195                 200                 205

Pro Ala Ser Ala Ser Ser Leu Pro Gly Asn Gly Ala Gln Leu Pro Pro
    210                 215                 220

Gln Pro Asp Thr Trp Ser Ser Pro Ser Pro Thr Leu Thr Thr Thr Pro
225                 230                 235                 240

Gly Ala Asp Gly Cys Glu Pro Gly Gly Arg Pro Ala Asp Cys Ser Pro
                245                 250                 255

Pro His Pro Ala Pro Ala Pro Gln His Pro Ala Ala Ser Ala Leu Arg
                260                 265                 270

Thr Arg Met Thr Gly Gly Arg Pro Pro Leu Pro Pro Pro Asp Asp Pro
            275                 280                 285

Ala Thr Leu Gly Pro His Leu Ala Ser Val Val Tyr Pro Arg Ala Gln
        290                 295                 300

Gln Pro Ala Arg Asp Pro Ala Pro Ser Leu Gly Pro Leu Leu Lys Ala
305                 310                 315                 320

Ile Pro Ser Pro Ile Trp Gly Pro Trp Ala Pro Ile Leu Ile Ser Leu
                325                 330                 335

Leu Asp Trp Asn Cys Cys Tyr Pro Ala Gly Val Gly Glu Ala Cys Thr
                340                 345                 350

Asp Trp Gly Leu Gly Gln Gly Gly Gln Gly Glu Gly Phe Gly Arg Ser
            355                 360                 365

Leu Pro Thr Lys Asp Trp Thr Leu Gly Pro Leu Ser Pro Phe Phe Ser
        370                 375                 380

Ile Tyr Cys Thr Lys Asp Ser Gly Gly Pro Val Glu Gly Arg Pro Pro
385                 390                 395                 400

Pro His Pro Arg Thr Leu Gly Gly Gly Gly Arg
                405                 410
```

<210> SEQ ID NO 5
<211> LENGTH: 27
<212> TYPE: DNA
<213> ORGANISM: Homo sapiens

<400> SEQUENCE: 5
gatcttgatg gccacaagct cctgggt                                        27

<210> SEQ ID NO 6
<211> LENGTH: 28
<212> TYPE: DNA
<213> ORGANISM: Homo sapiens

<400> SEQUENCE: 6
gtcaatttcg tagcgctcca ccagcgct                                       28